US012584093B2

(12) United States Patent
Piechocki et al.

(10) Patent No.: US 12,584,093 B2
(45) Date of Patent: Mar. 24, 2026

(54) PROCESS FOR MANUFACTURING LYSED CELL SUSPENSION

(71) Applicant: CORBION BIOTECH, INC., South San Francisco, CA (US)

(72) Inventors: John Piechocki, South San Francisco, CA (US); Cornelis Johannes Govardus Van Strien, Gorinchem (NL); Linda Wilhelmina Antonetta Claassen, Gorinchem (NL); Peter Johannes Marie Baets, Gorinchem (NL); Jorge Galazzo, South San Francisco, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 889 days.

(21) Appl. No.: 17/419,924

(22) PCT Filed: Jan. 3, 2020

(86) PCT No.: PCT/EP2020/050056
§ 371 (c)(1),
(2) Date: Jun. 30, 2021

(87) PCT Pub. No.: WO2020/141206
PCT Pub. Date: Jul. 9, 2020

(65) Prior Publication Data
US 2022/0081673 A1      Mar. 17, 2022

Related U.S. Application Data

(60) Provisional application No. 62/787,974, filed on Jan. 3, 2019.

(30) Foreign Application Priority Data

Feb. 15, 2019    (EP) .................................... 19157377

(51) Int. Cl.

| | |
|---|---|
| *C12N 1/06* | (2006.01) |
| *A23K 10/16* | (2016.01) |
| *A23K 20/158* | (2016.01) |
| *A23K 40/00* | (2016.01) |
| *A23K 50/80* | (2016.01) |
| *A23L 17/00* | (2016.01) |
| *C12N 1/066* | (2026.01) |
| *C12P 7/6458* | (2022.01) |
| *C12P 7/6472* | (2022.01) |

(52) U.S. Cl.
CPC .............. *C12N 1/066* (2013.01); *A23K 10/16* (2016.05); *A23K 20/158* (2016.05); *A23K 40/00* (2016.05); *A23K 50/80* (2016.05); *A23L 17/00* (2016.08); *C12P 7/6458* (2022.01); *C12P 7/6472* (2013.01); *A23V 2002/00* (2013.01)

(58) Field of Classification Search
CPC .......... C12N 1/066; C12N 1/06; A23K 10/16; A23K 20/158; A23K 40/00; A23K 50/80; A23K 10/30; A23L 17/00; A23V 2002/00; C12P 7/6472
USPC ........................................................... 426/2
See application file for complete search history.

(56) References Cited

U.S. PATENT DOCUMENTS

| | | |
|---|---|---|
| 2003/0100097 A1 | 5/2003 | Barclay |
| 2007/0082008 A1 | 4/2007 | Harel et al. |
| 2009/0093543 A1 | 4/2009 | Xue et al. |
| 2012/0204802 A1 | 8/2012 | Nichols et al. |
| 2018/0000130 A1 | 1/2018 | Rakitsky et al. |

FOREIGN PATENT DOCUMENTS

| | | | |
|---|---|---|---|
| GB | 2324701 A | * 11/1998 | ........... A23K 20/158 |
| WO | 96/33263 A1 | 10/1996 | |
| WO | 2010/107415 A1 | 9/2010 | |
| WO | 2012/021703 A1 | 2/2012 | |
| WO | 2015/095690 A2 | 6/2015 | |
| WO | 2018/005856 A1 | 1/2018 | |
| WO | 2018/122057 A1 | 7/2018 | |

OTHER PUBLICATIONS

NPL Particle size distribution (Retrieved on Dec. 13, 2023). (Year: 2023).*
NPL Solid Content Determination (Retrieved on Jul. 1, 2024). (Year: 2024).*
Ganuza et al.; "Cryptecodinium cohnii and Schizochytrium sp. as potential substitutes to fisheries-derived oils from seabream (Sparus aurata) microdiets;" Aquaculture; 2008; pp. 109-116; vol. 277.
Jan. 28, 2020 Search Report issued in International Patent Application No. PCT/EP2020/050056.
Jan. 28, 2020 Written Opinion of the International Searching Authority issued in International Patent Application No. PCT/EP2020/050056.

* cited by examiner

*Primary Examiner* — Erik Kashnikow
*Assistant Examiner* — Bhaskar Mukhopadhyay
(74) *Attorney, Agent, or Firm* — Sunit Talapatra; Foley & Lardner LLP

(57) ABSTRACT

A process for manufacturing a lysed cell in oil suspension and methods of applying thereof, the lysed cell in oil suspension including a solids content of at least 10 wt. % and a particle size Dv90 of 100 to 300 microns, including steps a) adding a first portion of microbial cell matter to an oil, b) subjecting the mixture of microbial cell matter and oil to one or more shear steps to effect lysis of at least part of the cells and produce a suspension including lysed cells in oil, c) adding a further portion of microbial cell matter to the suspension including lysed cells in oil, d) subjecting the mixture of microbial cell matter and the suspension including lysed cells in oil to one or more shear steps to effect lysis of at least part of the cells and produce a further suspension including lysed cells in oil.

19 Claims, 6 Drawing Sheets

Settings after 4 weeks post processing

| Low shear | Moderate Shear | High Shear |
|---|---|---|
| D90<1000 | D90<500 | D90<300 |

PROCESS FOR MANUFACTURING LYSED CELL SUSPENSION

This application claims benefit of priority under 35 U.S.C. § 119(e) to U.S. Provisional Patent Application No. 62/787,974, filed 3 Jan. 3, 2019, and to European Patent Application No. 19157377.3, filed 15 February, both titled "Process for Manufacturing Lysed Cell Suspension", which are incorporated herein by reference in their entirety.

The present invention pertains to a process for manufacturing a lysed cell suspension, in particular, a suspension of lysed cells in oil. The invention also pertains to a lysed cell suspension with specific properties which can be obtained through the process according to the invention.

WO2018005856 describes a process for manufacturing a composition comprising the steps of blending microbial cells and another oil source to form a blend, and lysing the microbial cells in the blend to form the composition as a dispersion.

As is explained in WO2018005856, triglyceride oils produced by microorganisms and plants provide essential nutrients for consumption by organisms higher in the food chain. Such triglyceride oils are composed of certain fatty acids that are not found or that are produced in lower amounts in the higher order organisms. Of particular nutritional importance in the food chain are triglyceride oils produced by microorganisms and plants that are high in polyunsaturated fatty acids (PUFA). Polyunsaturated fatty acids include long chain omega-3 fatty acids such as docosahexaenoic acid (DHA). DHA is an important component in human nutrition especially for infants. Aquatic animals such as fish and shellfish also require DHA in their diet for proper development and growth. Additionally, feeding DHA to newly born domesticated animals such as pigs, cows and other mammals increases the survival rate of piglets, calves, kids and other new-born mammals.

A major source of commercial long chain omega-3 fatty acids today is fish oil. About one million metric tons of fish oil are produced each year for use mainly for feed applications in aquaculture, terrestrial animal feed, and human nutrition. The aquaculture industry is growing, but the availability of long chain omega-3 fatty acids from wild caught fish has not increased with demand. Continued availability depends on sustainable fishery management policies, productivity of natural systems that are sensitive to climate changes, and other factors. Many countries have strict quotas on wild caught fish.

A particularly attractive source of long chain omega-3 fatty acids are microorganisms, in particular yeasts, fungi and algae. These microorganisms are often provided as spray-dried or drum-dried products. However, compositions of spray-dried or drum-dried microorganism are not always attractive, for a number or reasons. In the first place, dried microbial cells that contain high amounts of PUFA may need to be classified as self-heating. This means that manufacture, storage, and use of these compositions require safety measures. Additionally, dried cell mass has a low bulk density, which means that relatively large volumes are required to transport a given amount of cell mass. Further, due to the relatively large surface area of the dried cell mass, there is a substantial risk of interaction of the cells with oxygen from the air, which may lead to degradation.

These problems are solved by the provision of a suspension comprising lysed cells in oil, as described in WO2018005856. There is also a need to develop a large scale production process which is particularly suitable for providing a suspension with a high cell loading in the suspension, providing a higher concentration of valuable biomaterials (e.g., DHA or other omega-3 fatty acids) in the suspension. The present invention meets these and other needs.

The present invention provides a process which allows the manufacture of such suspensions in an economic and reproducible manner. In some embodiments, the present invention provides a high throughput process which is economical and further enables incorporation of a large amount of cells (i.e., high cell loading) in the suspension. It is advantageous to disperse large amounts of cells in oil to form the suspension comprising lysed cells, as this allows the manufacture of suspensions containing a large percentage of oil derived from the microbial cells, in particular DHA and/or other omega-3 fatty acids.

The invention also pertains to specific cell suspensions. Advantageously, the suspensions provided herein have a specific particle size distribution range. Without wishing to be bound by any theory, it is believed that a suspension comprising lysed cells with a particle size range of Dv90 value between 100 to 300 microns provides a physical stability to the suspension, resulting in a minimal settlement of particles in the suspension. Such property enables a long-term storage of the suspension with a minimal settlement and no (or minimal) hard packing of solids at the bottom of a storage container. It is easier to use such suspension later in time without having to input much energy to re-disperse the suspension prior to use. These advantageous properties of the suspension are also achieved when the solids content of the suspension are relatively high in the suspension.

SUMMARY OF THE INVENTION

The invention pertains to a process for manufacturing a lysed cell in oil suspension with a solids content of at least 10 wt. % and a particle size Dv90 value of 100 to 300 microns, comprising the steps of
  a) adding a first portion of microbial cell matter to an oil,
  b) subjecting the mixture of microbial cell matter and oil to one or more shear steps to effect lysis of at least part of the cells and produce a suspension comprising lysed cells in oil,
  c) adding a further portion of microbial cell matter to the suspension comprising lysed cells in oil,
  d) subjecting the mixture of microbial cell matter and the suspension comprising lysed cells in oil to one or more shear steps to effect lysis of at least part of the cells and produce a further suspension comprising lysed cells in oil.

In one embodiment, the microbial cell matter has a water content of less than 10 wt. %.

The invention pertains to a new lysed cell in oil suspension having a solids content of at least 10 wt. % and a particle size Dv90 value of 100 to 300 microns. The lysed cell in oil suspension produced by the present method generally has at least 70%, at least 75%, at least 80%, at least 85%, at least 90%, at least 95%, or at least 98% cell lysis.

The invention pertains to a composition comprising the lysed cell in oil suspension and one or more components useful in a feed. The invention also pertains to a feed product comprising the composition.

The invention further pertains to a process for manufacturing an impregnated pellet wherein the porous pellet is contacted with the composition of the present invention.

The invention further pertains to raising an animal comprising feeding an animal the feed product according to the invention.

The invention further pertains to sustainably producing a meat product by feeding an animal feed product according to the invention, wherein the meat product comprises an increased level of omega-3 fatty acids compared to the meat product produced without feeding the animal of the composition comprising the lysed cell in oil suspension.

The invention further pertains to a system comprising a low shear mixer, a high shear mixer, one or more pumps to produce a suspension comprising lysed cells, in particular a suspension of lysed cells in oil.

The embodiments of the invention provide many advantages. The present process can achieve a high cell biomass loading (e.g., 70-95 wt. % of the final lysed cell suspension being derived from microbial cell matter) and a high degree of cell lysis (e.g., at least 70%, 75%, 80%, 85%, 90%, 95%, or 98% cell lysis). It is noted that, as will be evident to the skilled person, the terms "biomass" and "cell matter" are used interchangeable herein.

The high percentage of cell lysis that can be achieved in the process according to the invention can be seen from the particle size distribution of the lysed cell in oil suspension obtained in the process according to the invention. The lysed cell suspension has a particle size Dv90 value of 100 to 300 microns. In some embodiments, the lysed cell suspension has a particle size Dv90 value of at most 260 microns, more in particular at most 240 microns, still more in particular at most 220 microns, in some embodiments at most 200 microns. In some embodiments, the particle size D90 value is 110 to 250 microns, optionally 120 to 200 microns. The particle size Dv90 value of less than 300 microns is required to prevent the solid particulates from settling out of suspension and hard packing, making them extremely difficult to resuspend without significant energy input to remix the suspension. Reference is made to FIG. 6, which shows the settlement behavior of suspensions with different particle size Dv90 values. On the other hand, lysed cells having a particle size Dv90 value that is too low may agglomerate. Processing of agglomerated lysed cells requires more energy than processing of lysed cells that have not agglomerated. Agglomeration of lysed cells is, thus, undesired. The particle size Dv90 value is determined using a Malvern Mastersizer 3000 laser diffraction particle size analyzer. More specifically, a sample of the lysed cell in oil suspension is dispersed in a shoutable, particle-free oil (e.g., rapeseed oil or soybean oil) and measured with a Malvern Mastersizer 3000, applying calculations according to the Mie theory.

The lysed cell in oil suspension with a higher cell biomass loading provides larger amounts of valuable biomaterial (e.g., DHA) per volume unit. The larger amounts of valuable biomaterial per volume unit enable a higher dosing of the biomaterial into feed products (e.g., via top coating onto feed pellets). The higher biomass loading per unit volume also lowers the transportation cost and greenhouse gas emissions. Furthermore, different types and/or amounts of antioxidants can be incorporated into the lysed cell in oil suspension (compared to the dry cell biomass) to increase the oxidative stability of the suspension. The current process is also capable of handling greater than 5000 kg/hour of cell matter intake, which is a desired capacity for the commercial scale production system.

The curve with a circle symbol with the lowest y-axis values at the bottom is a test sample of lysed cell in oil suspension derived from 50 wt. % microbial cell matter and 50 wt. % rapeseed oil. Other test samples of lysed cell suspension are derived from about 80 wt. % microbial cell matter and about 20 wt. % rapeseed oil. The particle size Dv90 value for the lower cell loading (the curve at the bottom) was 168 microns. The particle size Dv90 values for the higher cell loading samples were 139 microns, 155 microns, 151 microns, 159 microns, and 192 microns, respectively. These five different higher cell loading samples were generated under slightly different conditions (e.g., frequency of high shear varying from 30 Hz to 70 Hz; total number of passes varying from 10 to 35).

Figure 2:
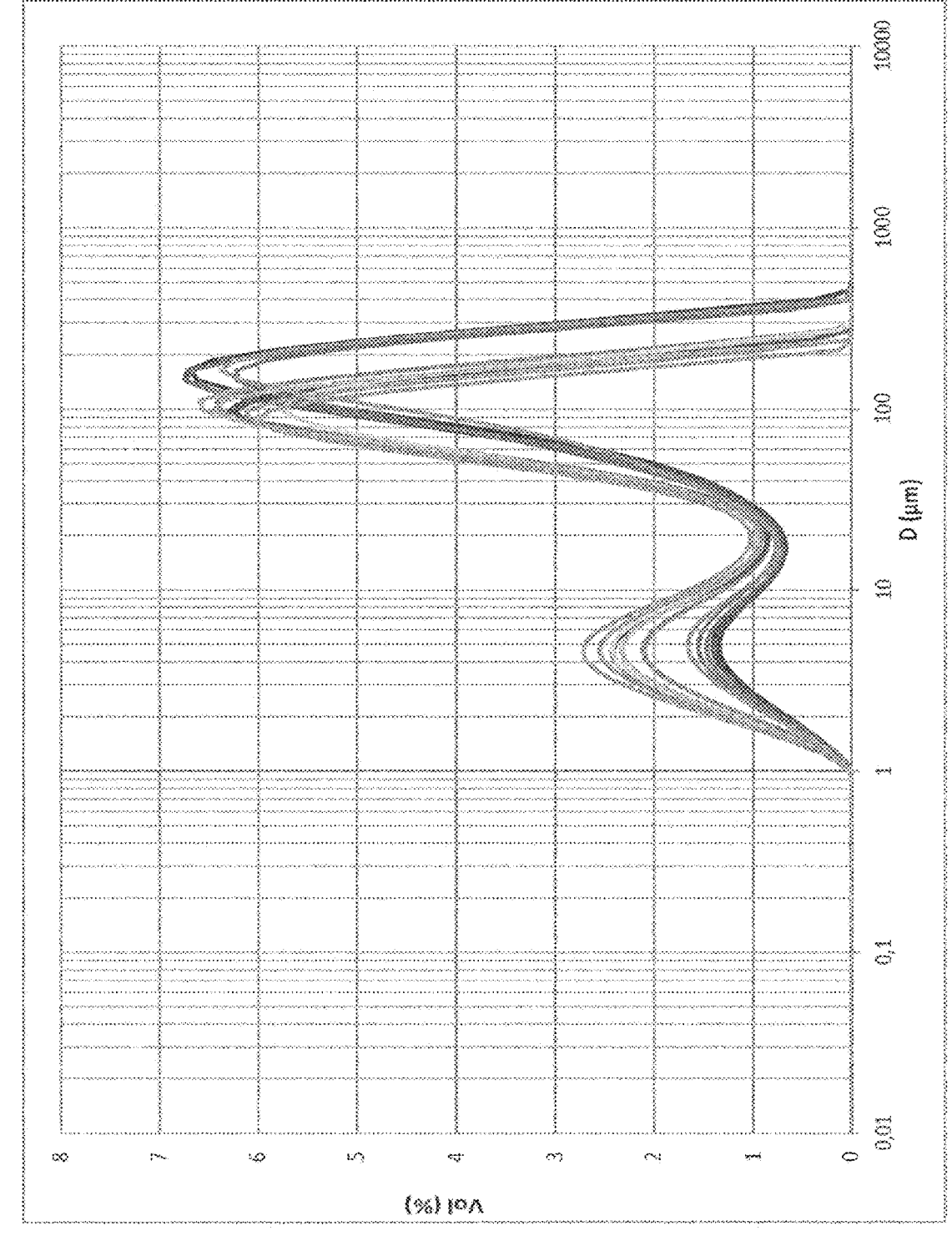

FIG. 2 shows the bimodal particle size distributions of the samples of lysed cell in oil suspension.

Figure 3:
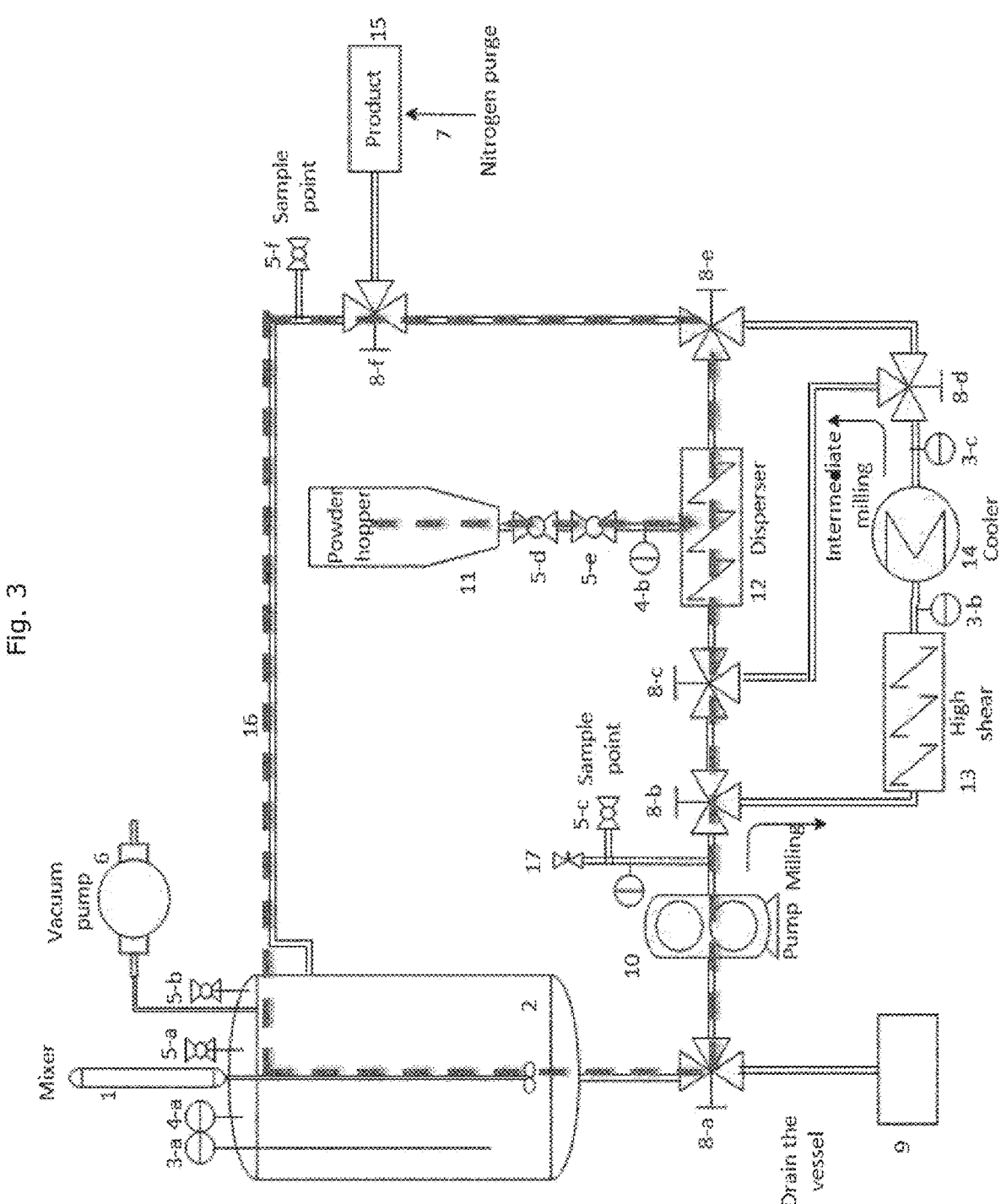

FIG. 3 shows a system according to one embodiment of the invention which shows a recirculation of a suspension of microbial cell matter and oil through a disperser 12 (i.e., a low shear mixer such as YTRON-ZC). The flow of the suspension is shown in a dashed line. Powder hopper 11 can be used to dose microbial cell matter into the system. Oil can be fed into mixer 2.

Figure 4:
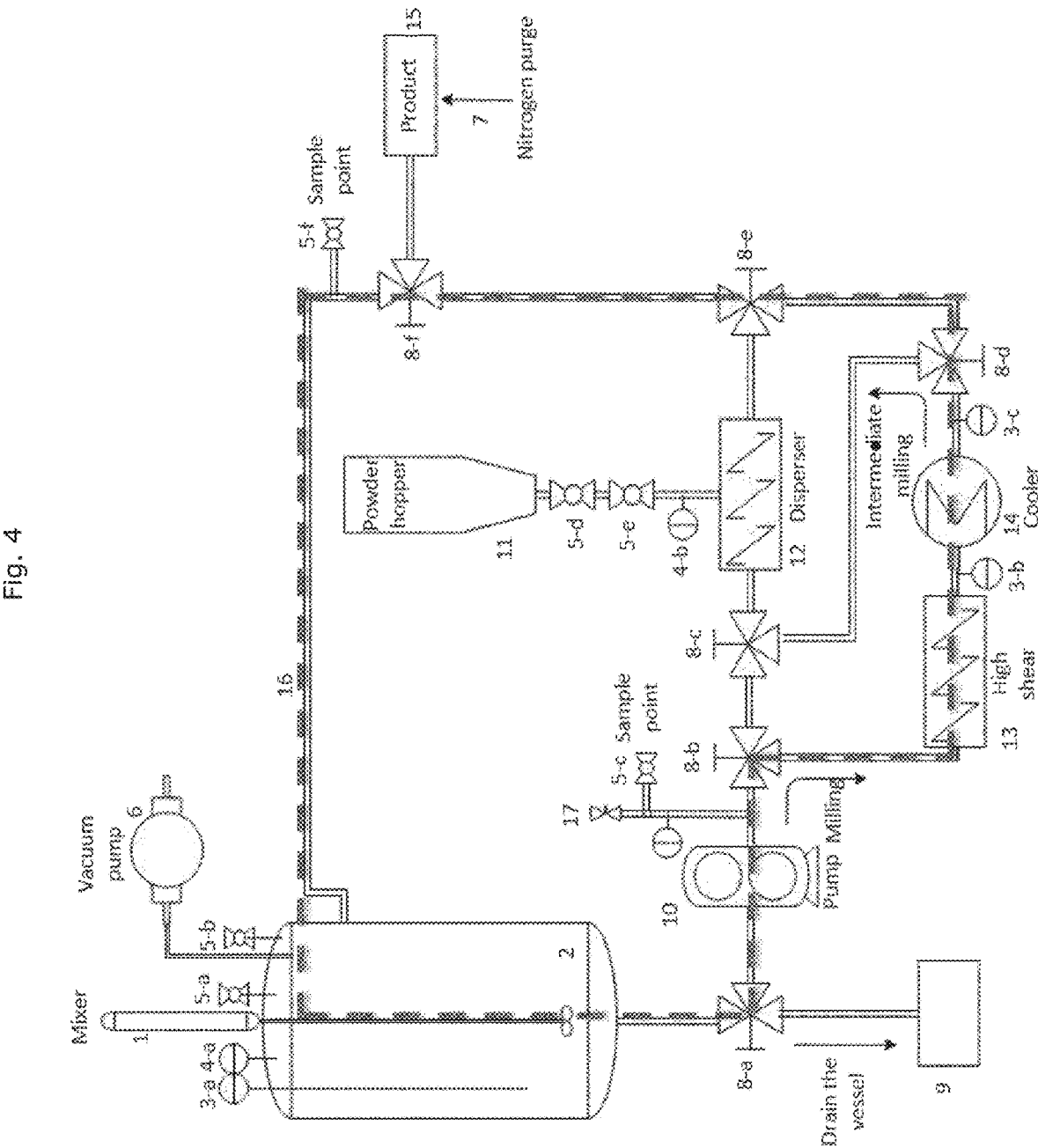

FIG. 4 shows a system according to one embodiment of the invention which shows recirculation of a suspension comprising lysed cells in oil through a high shear mixer 13 (such as YTRON Z) to lyse the cells in oil. The flow of the suspension is shown in a dashed line.

Figure 5:
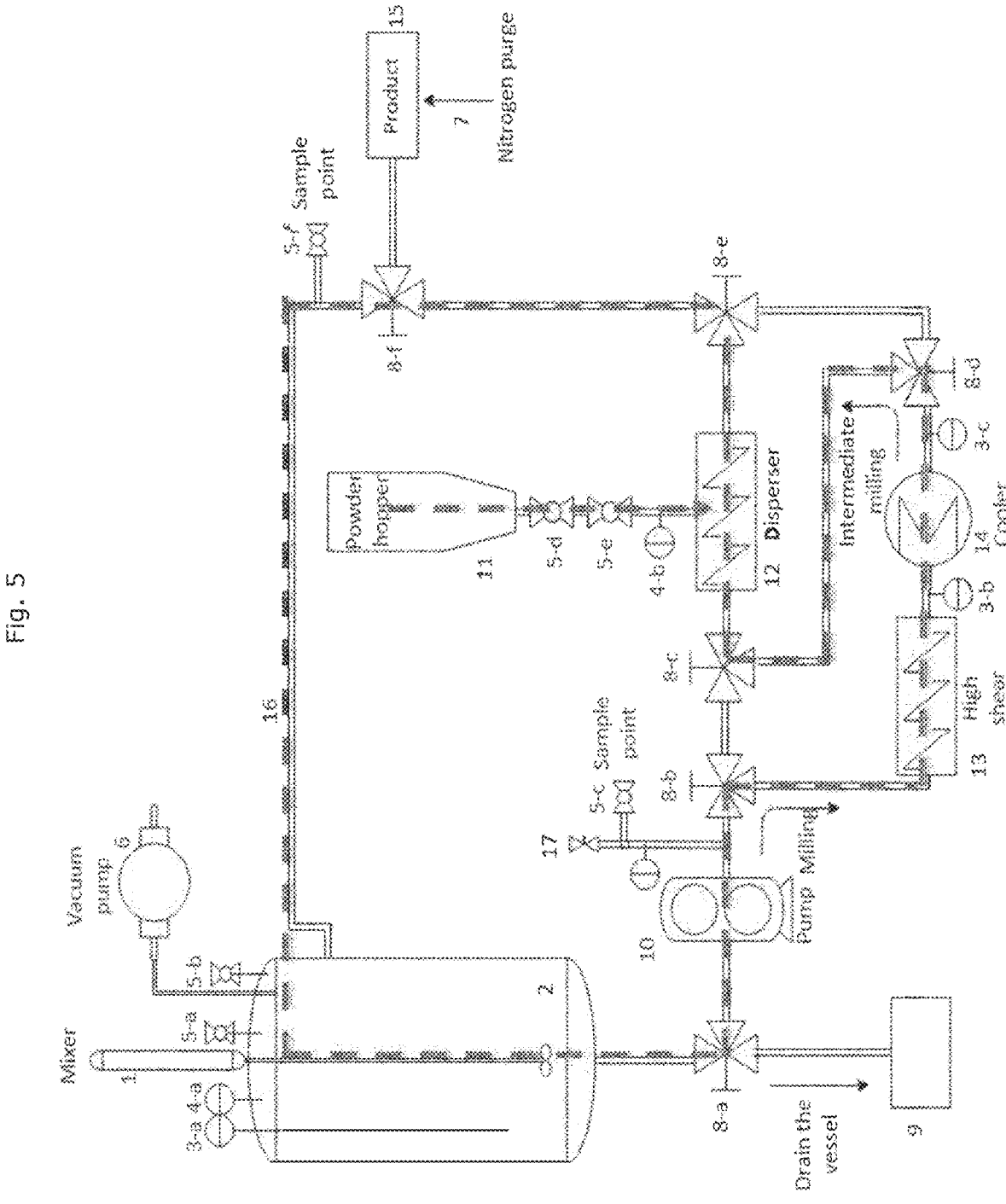

FIG. 5 shows a system according to one embodiment of the invention which shows dispersion of the microbial cell matter via a low shear mixer 12 and lysing of the cells in oil via a high shear mixer 13 in the same loop to produce a suspension. The flow of the suspension is shown in a dashed line.

Figure 6:
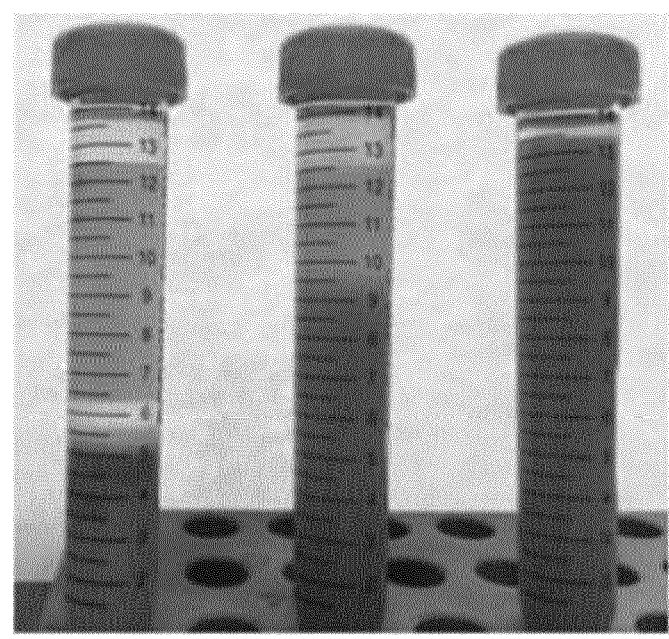

FIG. 6 shows the settling after four weeks post processing of suspensions with about 20% biomass and about 80% rapeseed oil that have been subjected to low shear, moderate shear or high shear conditions.

DETAILED DESCRIPTION OF THE INVENTION

The lysed cell in oil suspension produced by the process according to the invention is thus derived from microbial cells which are incorporated in an oil, and at least partially lysed, that is, the cell walls of some or most of the cells are disrupted and the oil from the lysed microbial cells is released. The solids content of the suspension is a measure for the amount of cell matter (e.g., cell debris and intact cells with oil) in the suspension. Solids content in wt. % is defined as follows:

$$\text{Solids content (wt. \%)} = 100\% - \text{water (wt. \%)} - \text{free oil (wt. \%)}.$$

The wt. % water is determined via Karl Fischer titration. The Karl Fischer procedure is a volumetric titration process used for the quantitative determination of water content in liquid and solid samples. The titration is carried out with titrant Hydranal Composite 2 (a one-component reagent which already contains all the reactants including iodine, sulfur dioxide, and the bases imidazole and 2-methylimidazole). Titration medium used is a mixture of dried dichloromethane (DCM) and dried methanol (ratio 75/25% v/v) The endpoint is determined using bivoltametric indication. i.e. the potential at the polarized double-platinum-pin electrode falls below a certain value, e.g., for a Mettler Toledo V30 KF Titrator with DM143-SC electrode and polarization current setting of 24.0 μA, the value is 100.0 mV.

The water content in the sample can be determined by the added amount of the reagent.

The wt. % free oil is determined as follows: Free oil (oil not bound within intact microalgal cells) present in the sample is extracted into a solvent layer, in this case hexane. The solvent/oil fraction is separated from the solids fraction by the addition of water and applying a centrifugal force (for at least 12000 RPM for 6 minutes). The hexane/oil partition is transferred to a tray which is placed in a fume hood. Hexane is evaporated at room temperature until stable, leaving only the free oil, the amount of which can be determined gravimetrically.

The process according to the invention makes it possible to obtain lysed cell in oil dispersions with relatively high solids content, e.g., at least 10 wt. %, at least 15 wt. %, in particular at least 20 wt. %, more in particular at least 25 wt. %, even more in particular at least 28 wt. %, in some embodiments at least 30 wt. %. In some embodiments, the invention makes it possible to obtain lysed cell in oil suspensions with between 15 wt. % and 45 wt. % solids content, in particular between 20 wt. % and 40 wt. % solids content, more in particular between 25 wt. % and 35 wt. % solids content.

As water may detrimentally affect the shelf life of the suspension, it is preferred for the final lysed cell suspension to have a water content of at most 10 wt. %, in particular at most 8 wt. %, more in particular at most 6 wt. %, even more in particular at most 4 wt. %, still more in particular at most 2 wt. %, even more in particular at most 1.0 wt. %. Water content is determined using the Karl Fischer Titration method described above.

In certain embodiments, the microbial cell matter, as the starting material, has a water content of less than 10 wt. %. In particular the microbial cell matter has a water content less than 8 wt. %, more in particular less than 6 wt. %, even more in particular less than 4 wt. %, still more in particular less than 2 wt. %, in some embodiments less than 1 wt. %. In particular, the microbial cell matter has a water content of between 0.5 wt. % to 8 wt. %, more particularly between 1 wt. % to 5 wt. %, even more particularly between 0.5 wt. % to 3 wt. %. The microbial cell matter provided as starting material of the process according to the invention may comprise whole and disrupted microbial cells. Depending on the source and optional pre-treatment steps, the cell matter provided as starting material to the process according to the invention generally comprises at least 10 wt. % of whole microbial cells, in particular at least 20 wt. %, more in particular at least 30 wt. %, or at least 40 wt. %, or at least 50 wt. %, or at least 60 wt. %.

The microbial cell matter with a water content in this range can be obtained in manners known in the art. For example, the microbial cell matter with a water content in the specified range can be obtained by subjecting a fermentation broth comprising microbial cells to a drying step. Drying of the microbial cells in the aqueous fermentation broth can, e.g., be accomplished by first optionally dewatering fermentation broth (concentrating the fermentation broth) to increase the cellular content of the broth. Dewatering or concentrating refers to the separation of the biomass from fermentation broth or other liquid medium and so is solid-liquid separation. Thus, during dewatering, the culture medium is removed from the biomass (for example, by draining the fermentation broth through a filter that retains the biomass), or the biomass is otherwise removed from the culture medium. Common processes for dewatering include centrifugation, filtration, evaporation, and the use of mechanical pressure. These processes can be used individually or in any combination. After the optional dewatering step, the concentrated broth, now with a higher solids content, can be dried by a known drying process, including but not limited to drum drying, pneumatic drying, spray drying, freeze drying, lyophilizing and other drying process.

A drum dryer operates by applying a film of the fermentation broth (or dewatered fermentation broth) to the surface of a rolling, heated drum. The aqueous portion of the broth evaporates leaving a dried solid on the surface of the drum. The dried solids are then scraped off the drum with a knife. Pneumatic dryers draw or entrain the material that is to be dried in a stream of hot air. While the material is entrained in the hot air, the moisture is rapidly removed. The dried material is then separated from the moist air and the moist air is then recirculated for further drying. A spray dryer operates by spraying the fermentation broth (or dewatered fermentation broth) in a fine droplet dispersion into a current of heated air. The entrained material is rapidly dried and forms a dry powder. Spray drying can be accomplished by a box-dryer, or a tall-form spray-dryer, a fluidized bed dryer, or a moving fluidized bed dryer (e.g., a FilterMat® spray dryer, GEA Process Engineering, Inc.).

In one embodiment, the microbial cells are oleaginous yeast cells, fungal cells, or microalgae cells. In some embodiments, the oleaginous yeast includes organisms such as *Yarrowia lipolytica, Rhodotorula glutinis, Cryptococcus curvatus* and *Lipomyces starkeyi*. In other embodiments, the microalgal cells include organisms from the family of Thraustochytriaceae and Crypthecodiniaceae. It may be preferred for the microbial cells to be from the genus selected from the group consisting of *Crypthecodinium, Ulkenia, Thraustochytrium, Aurantiochytrium,* and *Schizochytrium*. In one embodiment, *Schizochytrium limacinum* or *Aurantiochytrium limacinum* is used.

In some embodiments, microbial cells are oleaginous microorganisms capable of producing a large amount of lipids, in particular triglycerides. In certain embodiments, the microbial cells comprise at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, in particular between 40 wt. % to 75 wt. %, or between 45 wt. % to 67 wt. %, lipids, in particular triglycerides, calculated on dry biomass weight.

The selection of microbial cells depends on the biomaterial desired in the lysed cell in oil suspension. In one embodiment, microbial cells comprising a large amount of DHA can be used. In some embodiments, microbial cells comprise at least 15 wt. % DHA, at least 20 wt. % DHA, at least 25 wt. % DHA, at least 30 wt. % DHA, at least 35 wt. % DHA, at least 40 wt. % DHA, at least 45 wt. % DHA or optionally between 20 wt. % and 50 wt. % DHA, or between 20 wt. % and 45 wt. % DHA, or between 25 wt. % and 35 wt. % DHA, or between 25 wt. % and 45 wt. % DHA of the dry biomass weight.

In one embodiment, microbial cells rich in eicosapentaenoic acid (EPA) are used, alone or in combination, with microbial cells rich in DHA. In other embodiments, microbial cells which are capable of producing both DHA and EPA can be used. In some embodiments, the ratio of DHA to EPA in the microbial cells (either from the single microbial source or from multiple microbial sources) can be between 100:1 and 1:100, in particular between 10:1 and 1:10, more in particular between 4:1 and 1:4. In some embodiments, one or more microbial cells that produce arachidonic acid (ARA) are used, alone or in combination, with any of the microbial cells described herein.

In some embodiments, microbial cells are not transformed with transgenes. In other embodiments, microbial cells are genetically modified to produce one or more combinations and/or proportions of desired biomaterial in the microbial cells. A number of these microbial cells are either commercially available (e.g., ATCC deposits), or can be produced by methods known in the art. See, e.g., WO2012/021703, US20180000130, US2012204802, US20070082008, US2003100097, WO199633263, WO2010107415 and *Aquaculture* 277 (2008): 109-116.

In the present specification, the term "lipid" refers to any fat-soluble, lipophilic, naturally-occurring molecule. See US20090093543. The term "oil" refers to a lipid substance that is liquid at 25° C., and that is generally unsaturated. Oil is both hydrophobic and lipophilic, and is extractable in hexane. In oleaginous microbial cells, oil is the major component of the total lipid, and further, oil is composed primarily of triacylglycerol. Oil is distinguishable from semi-solid or solid fats which are not in the liquid state at a temperature of 25° C.

The term "triacylglycerols" refers to neutral lipids composed of three fatty acyl residues esterified to a glycerol molecule. Triacylglycerols contain long polyunsaturated fatty acids and saturated fatty acids, as well as shorter chain saturated and unsaturated fatty acids.

The term "neutral lipids" refer to lipids commonly found in cells in lipid bodies, and these lipids have no charged groups at cellular pH. Generally, they are completely non-polar with no affinity for water. Neutral lipids generally refer to mono-, di-, and/or triesters of glycerol with fatty acids, also called monoacylglycerol, diacylglycerol or triacylglycerol (collectively, acylglycerols). A hydrolysis reaction must occur to release fatty acids from acylglycerols.

The term "total fatty acids" refers to the sum of all cellular fatty acids (or fatty acids in a sample) that can be derivatized to fatty acid methyl esters ("FAMEs") by the base transesterification method in a given sample, which may be biomass, oil, lysed cell in oil suspension, for example. Thus, total fatty acids include fatty acids from neutral lipid fractions (including diacylglycerols, monoacylglycerols and triacylglycerols) and from polar lipid fractions (including, e.g., the phosphatidylcholine and phosphatidylethanolamine fractions) but not free fatty acids.

The term "total lipid content" of cells is a measure of total fatty acids as a percent of the dry cell weight ("DOW"), although total lipid content can be approximated as a measure of FAMEs as a percentage of DCW ("FAMEs % DCW). Thus, total lipid content (TFAs % DCW) is equivalent to, e.g., milligrams of total fatty acids per 100 milligrams of DCW.

The concentration of a fatty acid in the total lipid is expressed herein as a weight percent of TFAs (% TFAs), e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs (e.g., % DHA of total lipids is equivalent to DHA % of TFAs).

Suitable oils include oils derived from animals, plant, and oleaginous microorganisms such as microalgae, fungus, or yeast, or combinations thereof. In some embodiments, oil is used derived from plant material selected from coconut, corn, cottonseed, olive, palm, peanut, walnut, rapeseed, canola, safflower, sesame, soybean, soybean oil, sunflower, flaxseed, linseed, camelina oil, shea oil, or citrus oil, or one or more combinations thereof. These oils may be used in crude, unfiltered form, or may be used in any modified supply form (e.g., degummed and/or refined). In some embodiments, oil used is derived from a krill or a fish selected from herring, menhaden, anchovy, pilchard, sardine, or mackerel, tuna or one or more combinations thereof.

In some embodiments, oil extracted from microbial sources can be used to produce a lysed cell in oil suspension. In one embodiment, oil extracted from microbial cells is different from the source of microbial cells used to make a lysed cell in oil suspension. For example, the lysed cell in oil suspension can be produced by lysing *Schizochytrium* in oil extracted from *Crypthecodinium*. In another embodiment, oil extracted from the same organism can be used to make a suspension. For example, oil extracted from *Schizochytrium* rich in DHA can be added to the same *Schizochytrium* cell matter to produce a lysed cell in oil suspension. Such a suspension can further enrich the amount of desired biomaterial such as DHA in the suspension per unit volume. In some embodiments, extracted microbial oil may provide a source of other valuable endogenous biomaterials such as EPA, ARA, carotenoids, or astaxanthin.

In the process according to the invention, in one embodiment, a first portion of microbial cell matter with a water content of less than 10 wt. % is added to an oil.

In the process according to the invention, the microbial cell matter is combined with the oil in a portion wise manner, with intermediate lysis in one or more shear steps. The use of larger numbers of portions entails the addition of less cell matter per portion. This may make for better process control. On the other hand, the use of a larger number of portions makes for more process steps, which may be disadvantageous from a cost point of view. Accordingly, in some embodiments, in the process according to the invention, the total amount of cell matter is added in at least 2 portions and in general in at most 50 portions. It may be preferred to add the cell matter to the process in at most 40 portions, at most 30 portions, at most 25 portions, or at most 20 portions. It may be particularly preferred to add the cell matter in at most 15 portions, more in particular at most 10 portions. In some embodiments, it may be preferred to add the cell matter in at least three portions.

The size of the different portions may be the same or different. It may be preferred for the size of each portion to be at least 1 wt. % of the total amount of microbial cell matter added in the process, more in particular at least 2 wt. %. In general, the maximum portion size is at least 50 wt. % of the microbial cell matter added in the process. In some embodiments, the size of each portion can vary between 5 wt. % and 20 wt. %, or between 10 wt. % to 15 wt. %.

In one embodiment, microbial cell matter is added continuously to the oil. For example, microbial cell matter may be added continuously to a suspension comprising lysed cells in oil.

In the process according to the invention one or more shear steps are carried out after addition of a portion of microbial cell matter. The number of shear steps carried out after addition of a portion of microbial cell matter may vary within wide ranges. In one embodiment, a single step is carried out. In another embodiment, it is possible to carry out more than one shear step, e.g., a step at low shear which combines mixing and lysis followed by one or more steps at higher shear, or at increasing shear. In some embodiments, subsequent shear steps can be carried out in the same apparatus via recycling, e.g., by feeding a product a number of times through the same homogenizer, bead mill, or rotor-stator systems. In other embodiments, subsequent shear steps can also be carried out in different apparatus, e.g., in a number of sequential rotor-stator mixers. The total number of shear steps carried out after addition of a portion of microbial cell matter will generally be not more than 50.

Accordingly, in the process according to the invention, it is considered preferred to carry out the steps of adding a further portion of microbial cell matter to the suspension comprising lysed cells in oil, and subjecting the mixture of microbial cell matter and the suspension comprising lysed cells in oil to one or more shear steps to effect lysis of at least part of the cells and produce a further suspension comprising lysed cells in oil, at least one further time, in particular at least two further times.

The process according to the invention is carried out at a temperature at which the oil and the suspension are in the liquid phase. While there is no specific upper limit, higher temperatures may be less attractive because they may detrimentally affect the quality of the system. It may be preferred to carry out the process at a temperature below 80° C., preferably in the range of 10° C. to 60° C., more in particular in the range of 15° C. to 50° C., even more in particular in the range of 15° C. to 45° C. The temperature referred to here is product temperature. In some embodiments, oil is cooled in a tank prior to adding it to microbial cell matter to less than 25° C., less than 20° C., less than 15° C., or between 10° C. and 30° C.

When in the process according to the invention a first portion microbial cells matter has been added to the oil, the mixture of microbial cell matter and oil is subjected to a shear step to effect lysis of at least part of the cells in the oil.

In the present specification, the term "lysis" refers to a process wherein the cell walls of microbial cells are disrupted, and the oil content from the cells is released. The purpose of the process according to the invention is the provision of a suspension in which most of the microbial cells provided to the process have been lysed. In one embodiment, at the completion of the process according to the invention at least 70% of the cells provided to the process has been lysed, in particular at least 75%, in particular at least 80%, more in particular at least 85%, still more in particular at least 90%. In some embodiments at least 95 of the cells have been lysed, in particular at least 98%. In some embodiments, between 80% and 98% of the cells have been lysed, in particular between 85% and 98% of the cells have been lysed, more in particular between 85% and 95% of the cells have been lysed.

The percentage of cell lysis can be determined as follows. The percentage of lysis can be qualitatively determined under microscope visually, by observing and counting the number of lysed and unlysed cells in a sample.

Alternatively, the cell lysis percentage is determined by comparing the amount of free oil in a lysed cell suspension and the predetermined lipid content of the microbial cell matter (e.g., dried cell biomass).

Shear steps can be carried out in different processes and apparatus known in the art. Examples include roller mills, homogenizers, bead mills, shear mixers such as inline-mixers, waring blenders, and rotor-stator mixers. A French press or centrifugation may also be used, as may pumps and stirred vessels which provide shear.

The amount of shear to be provided in each step will depend on the total number of shear steps in the process. The higher the total number of shear steps, the less shear has to be provided in each individual step.

In one embodiment, a pressure disruptor, such as a high pressure homogenizer can be used to lyse the cells. A pressure disrupter lyses cells by pumping a mixture of cells and oil, e.g., canola oil or other plant oil, through a restricted orifice valve to lyse the cells. High pressure (from 50 bar up to 1500 bar) is applied, followed by an instant expansion through an exiting nozzle. A Niro (Niro Soavi GEA) homogenizer (or any other high pressure homogenizer) may be used. Processing of biomass with high pressure homogenizers can produce lysis of the cells to more than 50%, more than 60%, more than 70%, more than 80%, more than 90%, or more than 95% of the cells by controlling the pressure, exit velocity and other parameters.

Alternatively, a ball mill (also known as a bead mill) can be used. In a ball mill, cells are agitated in suspension with small abrasive particles, such as beads. Cells break because of shear forces, grinding between beads, and collisions with beads. The beads disrupt the cells to release cellular contents. Dyno-mill ECM Ultra (CB Mills) ball mill and other commercially available bead mills can be used. Processing of biomass in a ball mill can produce lysis of the cells to more than 50%, more than 60%, more than 70%, more than 80%, more than 90%, or more than 95% of the cells by controlling, among other features, the tip speed of the shaft, feed rate of the product through the mill, and/or the size and density of the beads.

In one embodiment, a rotor-stator mixer is applied in at least one of the shear steps. A rotor-stator mixer or system uses a rotating metal shaft (the rotor) inside a stationary metal casing (the stator). The rotation of the rotor creates a suction effect which draws the sample into the space between the rotor and stator, in which it is subject to shear forces due to the change in velocity in the small space between the rotor and stator. Centrifugal forces then push the material out through the slots in the stator, and the rapid motion of the fluid caused by the rotor-stator ensures that the process is repeated as the sample repeatedly cycle through it. In one embodiment a shear step is carried out in a series of rotor-stator mixers, e.g., between 2 and 10, in particular between 3 and 8, more in particular between 3 and 6. In this embodiment it may be preferred for at least one of the rotor stator mixers to have a narrower gap width than the preceding rotor stator mixer. It may be particularly preferred for each of the rotor stator mixers to have a gap width which is narrower than the gap width of the directly preceding rotor stator mixer. Processing of biomass with one or more rotor-stator mixers can produce lysis of the cells to more than 50%, more than 60%, more than 70%, more than 80%, more than 90%, or more than 95% of the cells by controlling, among other features, speed, gap width, the number of teeth on the rotor, and/or gaps between the teeth.

The degree of shear in a shear step in the process according to the invention can, e.g., be determined by way of the difference in lysed cell content in the cell/oil mixture provided to the shear step and the lysed cell content of the cell/oil mixture exiting from this shear step. In one embodiment, at least one shear step in the process according to the invention is carried out such that of the cells entering the shear step 1-60%, 5-50%, 10-40%, or 15-30%, 15%-25% is lysed.

In one embodiment, at least one shear step in the process according to the invention is carried out such that of the cells entering the shear step 80% is lysed, in particular at least 85%, more in particular at least 90%, still more in particular at least 95%, even more in particular at least 98%. To achieve the desired high degree of cell lysis in the process according to the invention it is preferred for the final shear step in the process according to the invention to be carried out under the conditions just specified. It is well within the scope of the skilled person to determine how a shear step is to be carried out to ensure that the desired degree of cell lysis is effected.

It may be preferred for at least one shear step in the process according to the invention to be carried out at higher shear than a preceding shear step. It may be preferred for the process according to the invention to comprise the steps of a) adding a first portion microbial cell matter to an oil, b) subjecting the mixture of microbial cell matter and oil to at least one shear step to effect lysis of at least part of the cells and produce a suspension comprising lysed cells in oil, wherein the combined set of one or more shear steps is carried out such that of the cells entering the combined set of one or more shear steps 1-60%, in particular 5-50%, more in particular 10-40%, even more in particular 15-30%, even more particular 15-25% is lysed upon exiting the combined set of one or more shear steps, c) adding a further portion of microbial cell matter to the suspension comprising lysed cells in oil, and optionally repeating step a), d) subjecting the mixture of microbial cell matter and the suspension comprising lysed cells in oil to at least one further shear step to effect lysis of at least part of the cells and produce a further suspension comprising lysed cells in oil, wherein combined set of one or more shear steps is carried out such that of the cells entering the combined set of one or more shear steps are at least 70% is lysed, at least 75% is lysed, at least 80% is lysed, in particular at least 85%, more in particular at least 90%, still more in particular at least 95%, even more in particular at least 98%.

In one embodiment, step b) is performed with one apparatus and step d) is performed with a different type of apparatus. For instance, step b) is performed in an apparatus which mainly incorporates microbial cells in oil, although some degree of cell lysis occurs during the incorporation or dispersion process. Any suitable disperser can be used. For example, it can be a low shear mixer, such as YTRON-ZC powder disperser. On the other hand, step d) is performed with a different apparatus which mainly lyses the cells to increase the percentage of cell lysis, decrease the particle size (e.g., Dv90), and to reduce viscosity of the suspension comprising lysed cells in oil. An example of a suitable apparatus in step d) includes YTRON-Z homogenizer which includes a rotor-stator system. Other suitable apparatus includes a powder incorporator and a rotor-stator system from IKA.

In one embodiment, step b) is performed in one or more shear steps. As used herein, "shear step" refers to a process step that causes disruption or breaking of the cell wall of microbial cells. While step b) is typically performed with a powder disperser, its low shear mixing causes some degree of cell lysis. After certain shear steps, a further portion of microbial cell is added to the mixture of microbial cells and oil as recited in step c). For example, in step b), between about 30-70 wt. %, in particular 40-60 wt. %, more in particular about 50 wt. % of microbial cells of the pre-weighted batch of microbial cell matter for the final lysed cell suspension can be added in 2-10 portions, in particular in 3-7 portions. Each portion can comprise about the same amount of microbial cell matter or different amounts of microbial cell matter. In some embodiments, after each portion is added to the suspension comprising lysed cells in oil, the suspension can be recirculated through the apparatus without further incorporating additional portions of microbial cell matter. In some embodiments, the suspension can be recirculated between 1 to 10 times, in particular between 3 to 8 times before further adding another portion of microbial cell matter.

As indicated above, a "shear step" refers to a process step that causes disruption or breaking of the cell wall of microbial cells. In particular, a shear step is a process step that causes at least 2% of the cells provided to the step to be lysed, in particular at least 5% in some embodiments at least 10%. In the present specification the term low shear step generally refers to a shear step in which 1-60% of the cells provided to the step is lysed, e.g., 2-60%, or 5-60%, or 10-60%. The term high shear step generally refers to a shear step in which more than 60% of the cells provided to the step is lysed.

When the lysed cell suspension is too viscous to be pumped through during step (b), the lysed cell suspension can be pumped into a higher shear step (d) to reduce its viscosity and to further lyse additional microbial cells. In an embodiment, after shearing steps (b) and adding further portion(s) of microbial cells (c) but before the lysed cell suspension is pumped into a higher shear apparatus in step (d), about 5-60%, in particular 10-40%, more in particular 15-30%, even more in particular 15-25% of microbial cells in the cell suspension are lysed.

In one embodiment, in step (d), the lysed cell suspension is pumped into a different apparatus which has a higher shear (e.g., a rotor stator system) than the apparatus used in step (b). In some embodiments, the lysed cell suspension is recirculated through the higher shear mixer apparatus between 1 and 50 times, in particular between 2 and 30 times, more in particular between 3 and 15 times until the cell particle size in the suspension is reduced and the viscosity of the lysed cell suspension is reduced. Once it is visually or quantitatively determined that the viscosity of the lysed cell suspension is reduced sufficiently, it is optionally returned to step (b) and (c) to add further portions of the remaining or additional pre-weighted microbial cell matter for the suspension.

Once the lysed cell suspension is returned to the low shear step (b), one or more further portions of microbial cells are incorporated into the lysed cell suspension. In one embodiment, at this stage, the remaining portions of the microbial cell matter can be added in any suitable amount of increments, for example, 1-10 portions, in particular 2-8 portions, or more in particular 3-6 portions. Each portion can comprise about the same amount of microbial cell matter or different amounts of microbial cell matter. After each portion is added to the suspension comprising lysed cells in oil, in one embodiment, the suspension can be recirculated through the apparatus without further incorporating additional portions of microbial cell matter. In some embodiments, the suspension can be recirculated between 1 to 10 times, in particular between 3 to 8 times before further adding another portion of microbial cell matter.

After the remaining portions are added (or if the cell suspension is too viscous to further mix additional portions of microbial cells) into the lysed cell suspension, the lysed cell suspension is returned to the higher shear mixer apparatus in step (d). In step (d), the lysed cell suspension is recirculated through the apparatus until a desired viscosity and/or cell particle size Dv90 value is achieved. In some embodiments, the further lysed cell suspension is passed through the apparatus in step (d) between 1 to 50 times, in particular 3 to 30 times, more in particular 5 to 15 times.

During any steps in (a) through (d), antioxidant(s) can be added at any stage in the process. However, it is advantageous to add antioxidant(s) near the beginning of the process to provide protection from thermal degradation of the oil by the heat of processing and any oxygen that may be introduced as a result of processing.

During any steps in (a) through (d), one or more pumping steps can be added to facilitate recirculation of the suspension in a continuous system. In certain embodiments, vacuum pumping steps can be added to facilitate dispersion of the microbial cell matter in oil. In certain embodiments, two or more different types of apparatus are connected in-line in the continuous system. Instead of recirculating the cell suspension into the same apparatus, two or more of the same apparatus can be connected in-line to pass the suspension through multiple apparatus instead of recirculating it through the same apparatus.

During any steps in (a) through (d), one or more cooling steps can be added to cool the lysed cell suspension. In one embodiment, a cooling step is added after a higher shear step (d). In one embodiment, the cooling step allows the suspension to maintain its temperature at or below 80° C., at or below 70° C., at or below 60° C., or at or below 50° C., in particular at or below 40° C., more in particular at or below 35° C., in some embodiments at or below 30° C.

The end product (i.e., the final lysed cell suspension) has a solids content of at least 10 wt. %, at least 15 wt. %, in particular at least 20 wt. %, more in particular at least 25 wt. %, even more in particular at least 28 wt. %, in some embodiments at least 30 wt. %, in some embodiments between 20 wt. % and 40 wt. %, in some embodiments between 25 wt. % and 35 wt. %.

The final lysed cell in oil suspension has a particle size Dv90 value of 100 to 300 microns. The final lysed cell in oil suspension may, in particular, have a Dv90 value of at most 260 microns, more in particular at most 240 microns, still more in particular at most 220 microns, in some embodiments at most 200 microns. In some embodiments, the final cell suspension has a particle size Dv90 value of between 110 microns and 250 microns, more in particular between 120 microns and 200 microns.

In some embodiments, the final lysed cell in oil suspension has a particle size Dv50 value of less than 150 microns. The final lysed cell in oil suspension may, in particular, have a particle size Dv50 value of at most 130 microns, more in particular at most 100 microns, even more in particular at most 80 microns. In some embodiments, the final cell suspension has a particle size Dv50 value of between 20 and 150 microns, in particular between 30 microns and 100 microns, more in particular between 40 microns and 80 microns. As will be evident to the skilled person, the particle size Dv50 value will always be smaller than the particle size Dv90 value for the same distribution of particles.

In some embodiments, a process of using two different types of apparatus is particularly useful in producing a lysed cells in oil suspension with both high solids content and a high degree of cell lysis. For example, the process can produce a final lysed cell suspension which is derived from 70-95 wt. % microbial cell matter and 5 wt. % to 30 wt. % added oil, in particular which is derived from 75-85 wt. % microbial cell matter and 15-25 wt. % added oil, and more in particular which is derived from 80 wt. % microbial cell matter and 20 wt. % added oil.

In one embodiment of the process according to the invention, microbial cell matter is added at a rate of at least 1000 kg/hour. This allows commercial scale production of suspensions. It may be preferred to add microbial cell matter at a rate of at least 2000 kg/hour, in particular at least 3000 kg/hour, more in particular at least 4000 kg/hour, in some embodiments at least 5000 kg/hour. The maximum for the addition rate of microbial cell matter is not critical. As a general value, a maximum of 20.000 kg/hour may be mentioned. Depending on commercial requirements, a rate of 1000 kg/hour to 20.000 kg/hour, in particular 2000 kg/hour to 15.000 kg/hour, more in particular 3000 kg/hour to 10.000 kg/hour, or 4000 kg/hour to 8000 kg/hour, for example between 5000 kg/hour and 6000 kg/hour of microbial cell matter may be preferred.

In one embodiment, the total energy input (to the low shear mixer, the high shear mixture, and pump) to generate the final lysed cell suspension can be between 0.01 and 0.2 kW*Hr/kg, in particular between 0.02 and 0.18 kW*Hr/kg, more in particular between 0.03 and 0.16 Kw*Hr/kg, and still in particular between 0.04 and 0.13 kW*Hr/kg, or any numbers between these ranges. As used herein, kilograms of weight refers to the weight of both microbial cell matter and added oil in the system. In an embodiment, the total energy consumption of the process (for incorporating the biomass in the liquid and applying shear) is between 0.050 and 0.150 kW*Hr/kg suspension, in particular between 0.060 and 0.130 kW*Hr/kg, more in particular between 0.070 and 0.120 kW*Hr/kg. The total energy consumption of the process (for incorporating the biomass in the liquid and applying shear) may be between 0.050 and 0.100 kW*Hr/kg suspension, in particular between 0.060 and 0.090 kW*Hr/kg. Alternatively, the energy consumption of the process (for incorporating the biomass in the liquid and applying shear) may be between 0.090 and 0.130 kW*Hr/kg suspension, in particular between 0.100 and 0.120 kW*Hr/kg.

In one embodiment, as described above, the shearing steps can be performed using two different types of shearing apparatus alternatively, for example as shown in FIGS. 3 and 4. In another embodiment, both pieces of shearing apparatus can be used concurrently in the same loop, for example as shown in FIG. 5.

While the above process describes shearing steps using two different types of apparatus, the process according to the present invention is not limited to using two types of apparatus for shearing steps. In some embodiments, a single type of apparatus can be used for shearing steps to produce a lysed cell in oil suspension. An example of such a process is provided in Example 3. In other embodiments, more than two (e.g., three, four, five, or more) types of apparatus can be used for shearing steps to produce a lysed cell in oil suspension.

The above process describes adding the microbial cell matter to oil. As indicated above, microbial cell matter encompasses both whole cells and disrupted cells. Cell disruption may, e.g., have taken place through milling or other pretreatment steps which cause some cell disruption.

The invention also pertains to new lysed cell in oil suspensions. The new cell in oil suspensions according to the invention have a solids content of at least 10 wt. % and a Dv90 of 100 to 300 microns. It is preferred for the lysed cell in oil suspension to have a solids content of at least 15 wt. %, in particular at least 20 wt. %, more in particular at least 25 wt. %, even more in particular at least 28 wt. %, in some embodiments at least 30 wt. %, in some embodiments between 20 wt. % and 40 wt. %, in some embodiments between 25 wt. % and 35 wt. %

As water may detrimentally affect the shelf life of the suspension It is preferred for the lysed cells in oil suspension to have a water content of at most 10 wt. %, in particular at most 8 wt. %, more in particular at most 6 wt. %, even more in particular at most 4 wt. %, still more in particular at most 2 wt. %, even more in particular at most 1.0 wt. %. Water content is determined as described above according to the Karl Fischer water determination method. It may be preferred for the lysed cell in oil suspension to have a particle size Dv90 value of at 300 microns, at most 260 microns, more in particular at most 240 microns, still more in particular at most 220 microns, in some embodiments at most 200 microns.

In one embodiment, the lysed cell in oil suspension has a particle size Dv50 value in the range of 20-150 microns. The lysed cell in oil suspension may, in particular, have a particle size Dv50 value in the range of 30-120 microns. The particle size Dv50 value is determined in the Malvern Mastersizer 3000 as described for Dv90.

In one embodiment, the lysed cell in oil suspension has a density of at least 0.95 g/ml. In some embodiments the density may be at least 1.00 g/ml, or even at least 1.05 g/ml. This relatively high density for an oil composition is associated with the relatively high solids content of the suspension (e.g., at least 25 wt. % or at least 30 wt. % solids content). The density of added oil, in particular vegetable oil, is typically around 0.9 g/ml. Therefore, with a higher solids content, the density of a lysed cell suspension is at least 7%-20%, in particular at least 8%-16%, or at least 10% greater than the density of the carrier oil itself added to the suspension. If the lysed cell suspension has a lower biomass loading and a lower solids content (e.g., suspension derived from 20 wt. % microbial cell matter and 80 wt. % added oil), then the density of the lysed cell suspension would be similar to that of the added oil (e.g., 0.92 g/ml to 0.95 g/ml). The higher solids content in the lysed cell suspension can further provide an advantage of providing a large quantity of valuable biomaterial, such as DHA, per volume unit, and a lower transportation cost for the final suspension.

Figure 1:
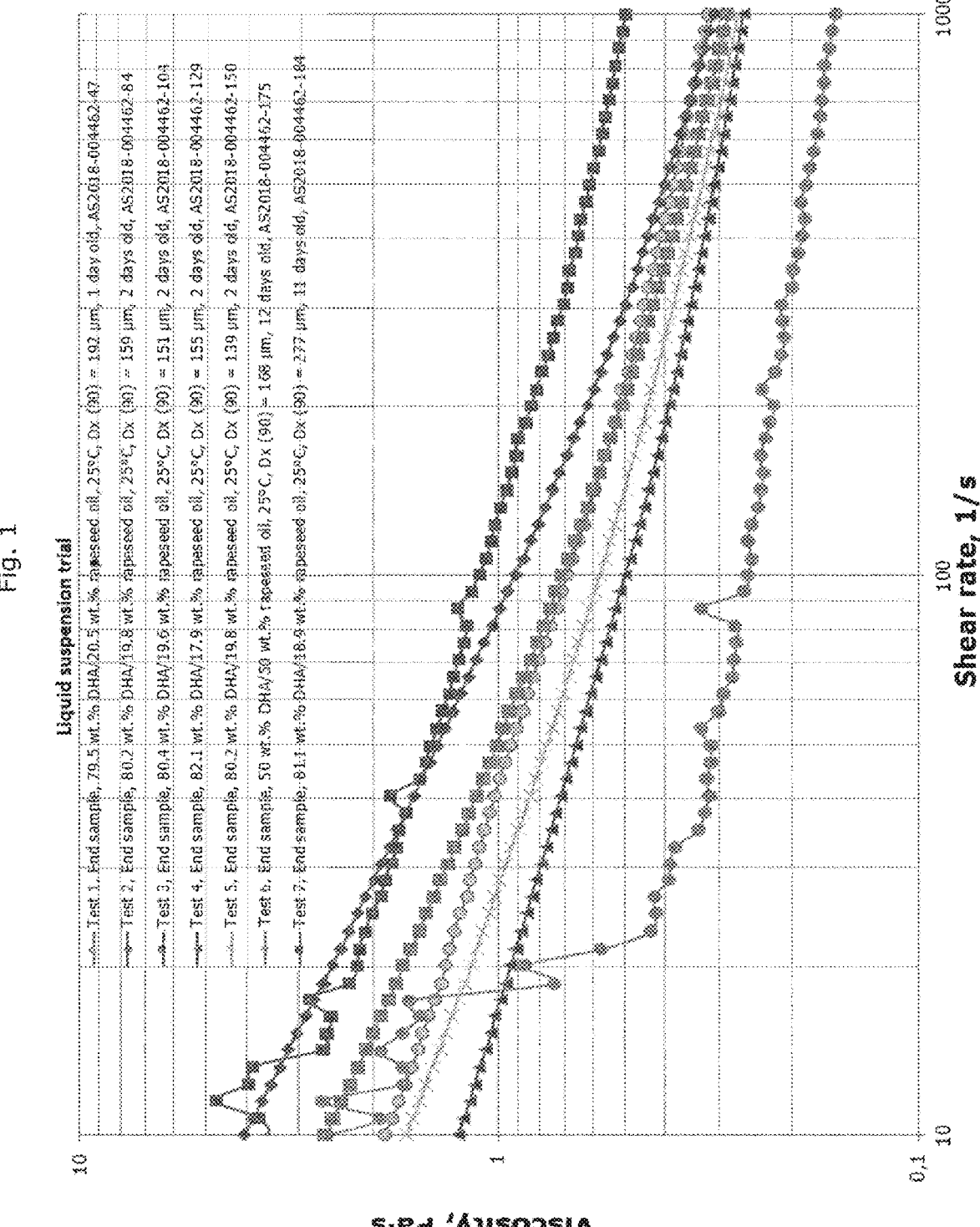
FIG. 1 shows shear rate (1/s) vs. viscosity (Pa·s) of six different samples of lysed cell in oil suspensions at 25° C.

An exemplary relationship between viscosity and shear rate of a suspension is shown in FIG. 1 for one embodiment. As will be evident to the skilled person, in the figure, Dx(90) is the Dv(90) and DHA refers to microbial cell matter. In this example, the suspension was derived from about 80 wt. % microbial cell matter and about 20 wt. % carrier oil. In this particular example, the suspension comprised about 32 wt. % solids content. In some embodiments, a suspension comprising lysed cells in oil has a viscosity of at most 3 Pa·s at shear rate of 100/s, in particular at most 2 Pa·s at shear rate of 100/s, more in particular at most 1 Pa·s at shear rate of 100/s. At the shear rate of 100/s, the viscosity of the suspension with a high solids content is at least 40% greater, at least 50% greater, at least 100% greater, at least 150% greater, at least 200% greater than the viscosity of a suspension with a lower cell biomass loading (50 wt. % microbial cell matter and 50 wt. % added oil). See FIG. 1. The viscosity was measured with a rheometer (Anton Paar, MCR301, spindle CC27, 25° C. and 40° C., shear 1 $s^{-1} \rightarrow 1000 \ s^{-1}$, followed by $1000 \ s^{-1} \rightarrow 1 \ s^{-1}$. More shear results in lower viscosity (at $100 \ s^{-1}$).

In some embodiments, the viscosity of the lysed cell suspension (as measured at 20° C.) is between 10 and 100,000 mPa·s, in particular between 100 and 50,000 mPa·s. The viscosity of the lysed cell suspension may be between 10 and 100,000 mPa·s, in particular between 100 and 50,000 mPa·s, after 60 days. Additionally or alternatively, the viscosity of the lysed cell suspension may be between 10 and 100,000 mPa·s, in particular between 100 and 50,000 mPa·s, after 143 days.

In some embodiments, the viscosity of the lysed cells suspension remains stable over time. For example, the viscosity after 30 days deviates less than 10% from the viscosity of the freshly prepared suspension, preferably less than 5%, more preferably less than 3%. Additionally or alternatively, the viscosity after 60 days may deviate less than 10% from the viscosity of the freshly prepared suspension, preferably less than 5%, more preferably less than 3%. The viscosity after 143 days may deviate less than 10% from the viscosity of the freshly prepared suspension, preferably less than 5%, more preferably less than 3%.

In one embodiment the lysed cell suspension has a DHA content of at least 10 wt. %, in particular at least 15 wt. % DHA, more in particular at least 18 wt. % DHA, still more in particular at least 22 wt. % DHA, calculated in wt. % on the total fatty acid content of the lysed cell in oil suspension. In some embodiments, the DHA content may be even higher, in particular in the case that the oil also contains DHA. For example, the DHA content may be at least 30 wt. %, in particular at least 35 wt. %, more in particular at least 40 wt. %, in some embodiments between 20 wt. % and 45 wt. %, in some embodiments between 25 wt. % to 35 wt. %.

In one embodiment, the suspension comprising lysed cells in oil further comprises an antioxidant. Examples of suitable antioxidants include natural or synthetic antioxidants. In some embodiments, the antioxidant is lecithin, starch, ascorbic acid, tocopherols, rosemary extract, green tea extract, ascorbyl palmitate butylated hydroxytoluene (BHT), butylated hydroxyanisole (BHA), tert-butylhydroquinone (TBHQ), ethoxyquin, or one or more combinations thereof. In some embodiments, the suspension comprising lysed cells in oil does not include ethoxyquin as an antioxidant. Because the suspension comprising lysed cells in oil has less surface area than dried cellbiomass, it has a longer shelf life with either natural or synthetic antioxidants at lower levels than needed in the dried cell biomass.

In another embodiment, the lysed cell suspension is combined with one or more components to produce a composition suitable for inclusion into a feed. As used herein, the term "feed" includes any food product for an animal, such as a terrestrial animal feed including human food product, or an aquaculture feed product. The terrestrial animal feed product may be a monogastric or ruminant animal feed product. The terrestrial animals can include cattle (e.g., dairy cows or beef cattle) fowls (e.g., broilers or hens). The feed can also include food products for companion animals. The aquaculture feed product includes those for fish or shell fish (e.g., salmon, trout, or shrimp). In some embodiments, one or more components can be additional oil which is added to the lysed cell in oil suspension at the site of feed production. For example, the additional oil can be any one of coconut, corn, cottonseed, olive, palm, peanut, walnut, rapeseed, canola, safflower, sesame, soybean, soybean oil, sunflower, flaxseed, linseed, camelina oil, shea oil, or citrus oil, or one or more combinations thereof. The additional oil can be also derived from a fish, krill, or microorganisms. In some embodiments, the additional oil can be same as the oil incorporated into the lysed cell suspension. In other embodiments, the additional oil can be different from the oil incorporated into the lysed cell suspension. In some embodiments, the one or more components can include other additives useful in the aquaculture or in terrestrial animal feed, such as astaxanthin, carotenoids, flavonoids, lecithin, sterols, calcitriols (vitamin D), tocopherols (vitamin E), and phylloquinone and menaquinone (vitamin K), antibiotics, antifungals, antiparasitics, and hormones. In other embodiments, the one or more components can include sources of omega-3 or omega-6 fatty acids, such as DHA, EPA, and/or ARA.

In some embodiments, lysed cell in oil suspension can be blended with dry ingredients and provided as feed or food as is without further processing. In other embodiments, the lysed cell in oil suspension can be blended with wet food ingredients prior to packaging them into feed or food products.

In some embodiments, the composition comprising the lysed cell in oil suspension is coated onto, or pressed or extruded with feed pellets. In some embodiments, the pellets are porous. The porous pellets can be impregnated with the lysed cell in oil suspension or a composition thereof. Any suitable contacting methods can be used to impregnate the porous pellets. These include, for example, top-coating, spraying, or vacuum coating. In an embodiment, the particle size Dv90 value of the lysed cell in oil suspension is not more than 20%, 10%, or 5% greater than the average pore size of the porous pellets. In another embodiment, the particle size Dv90 of the lysed cell in oil suspension is equal to or less than the average pore size of the porous pellets. The particle size Dv90 value of the lysed cell in oil suspension is between 100 microns and 300 microns, optionally between 110 microns and 250 microns, optionally between 120 microns and 200 microns. In some embodiments, the lysed cell suspension or the composition thereof can be incorporated with other feed ingredients to extrude or manufacture feed products.

Any suitable amount of the lysed cell in oil suspension can be incorporated into a feed product. In one embodiment, 0.5 wt. %-20 wt. %, optionally 1 wt. %-10 wt. %, more optionally 2 wt. % to 8 wt. % of the feed product is derived from the microbial cell matter.

In some embodiments, a method of raising an animal is provided. The method of raising an animal includes feeding an animal the feed product comprising lysed cell in oil suspension. The method can further comprise adjusting the amount of lysed cell suspension in the feed product during different lifecycle periods of the animal as needed. In some embodiments, an animal obtained by a method of raising an animal is provided.

In some embodiments, a method of sustainably producing a meat product is provided. The method comprises feeding an animal the feed product comprising a lysed cell in oil suspension or a composition thereof. The method can further provide an increased level of omega-3 fatty acids (e.g., DHA and/or EPA) compared to the meat produced without feeding the animal the lysed cell in oil suspension or the composition thereof. In some embodiments, meat product obtained by the method of sustainably producing a meat product is provided.

It will be clear to the skilled person that various embodiments of the present invention can be combined as desired, unless they are mutually exclusive.

The invention will be elucidated with reference to the following examples, without being limited thereto or thereby.

EXAMPLES

Example 1. Microbial Cells

DHA (docosahexaenoic acid) rich *Schizochytrium* cells were prepared by standard heterotrophic fermentation and dried using a drum dryer. The dried cell biomass contained about 60 wt. % oil. The dried cell biomass generally contained less than 5% water content, typically less than 2% or less than 1% water. The dried DHA rich *Schizochytrium* biomass is also commercially available as AlgaPrime™ DHA (Corbion Biotech, Inc., South San Francisco, USA).

Example 2. Measurement of Total Fatty Acids or DHA in Lysed Cell Suspension or Cell Biomass Samples were analyzed for fatty acid composition by converting them to FAMEs using direct transesterification.

Samples (10-20 mg) were weighed directly into 16×100 mm test tubes with PTFE-lined screw caps, followed by 200 uL of a 20 mg/mL solution of C19:0 internal standard (NuChek Prep, Inc, Elysian, MN) and 2 mL of 5% sulfuric acid in methanol containing 0.5% BHT. The tubes were capped and placed in a dry bath maintained at 75° C. for 3.5 h and vortexed and sonicated in a sonicator bath heated to 75° C. twice intermittently during the course of the transesterification. Sample tubes were removed from the dry block, and once cooled to room temperature, 2 mL of 10% potassium phosphate tribasic and 2 mL of heptane were added to the tube. The sample tubes were agitated vigorously with inversion and then centrifuged at 1600 rpm for 2 min to provide two distinct layers. A suitable portion of the upper layer was transferred to a sample vial or vial insert which contained sodium sulfate (anhydrous) lining the bottom, for analysis by GC-FID. FAMEs were quantified using empirical relative response factors (ERRF) for each FAME identified relative to the C19:0 internal standard, following the acceptable ERRF criteria guidelines outlined in AOCS method Ce 1i-07.

Example 3. Production of Lysed Cell in Oil Suspension Using a Single Type of High Shear Mixer A lysed cell in oil suspension was produced by lysing dry *Shizochytrium* biomass described in Example 1 in vegetable oil (e.g., rapeseed oil) using a single piece of equipment. In this example, a high shear mixer was used to add, wet, disperse, and lyse the cell biomass in oil under vacuum. The cell biomass (about 80% of the weight of the final product) was added continuously through a single piece of equipment. Rapeseed oil (about 20% of the weight of the final product) was added to a feed tank. The oil was pumped from the bottom of the tank and was injected into the equipment. The cell biomass from a separate hopper was introduced concurrently into the piece of equipment. The oil and cell biomass mixture was pumped back into the top of the tank. This process continued without pause until all of the preweighed microbial cells were incorporated into the oil. At this point, the oil and cell biomass mixture was continuously recirculated through the same piece of equipment until maximum lysis (e.g., between 80-90% cell lysis) and smallest Dv90 particle size was achieved (3 complete turnovers of the entire batch/tank). During this process, the speed of the shear mixer varied between approximately 2500 to 3600 revolution per minute. Continued processing did not result in much additional lysis or reduction in particle size. The particle size Dv90 value was less than 300 microns. The particle size Dv50 value was less than 150 microns. The solids content of the resulting lysed cell suspension produced by this method was approximately 32 wt. %. The water content of the lysed cell in oil suspension was less than 5 wt. %, typically less than 1 wt. %.

Example 4. Production of Lysed Cell in Oil Suspension Using Two Different Types of Shear Mixers A lysed cell in oil suspension was produced by mixing the dried microbial cells from Example 1 with vegetable oil (e.g., rapeseed oil) using two different equipment—the YTRON-ZC powder dispersing system (i.e., a low shear mixer) and the YTRON-Z high shear mixer (also referred to as a inline homogenizer) (YTRON Process Technology GmbH &Co. KG, Germany). The low shear mixer (optionally applying vacuum using a vacuum pump 6 shown in FIG. 3) was mainly used to incorporate or disperse microbial cells (in the powder form) into oil. After the microbial cells were dispersed into the oil, the mixture was pumped into a high shear mixer which was mainly used to lyse the cells and to reduce their particle size. The YTRON-Z houses rotor/stator sets. The parameters such as slot width, distance between the shear slots, the number of rotor/stator sets, rotation speed and flow rate, and/or energy input were varied to produce a desired dispersing or lysing effects. The pumps were used to invoke the recycle flow, making it possible to set the recycle flow independently from the other pieces of equipment (e.g., YTRON-Z or YTRON-ZC) in the recycle loop. The resulting lysed cell suspension was cooled over a heat exchanger and recycled over the high shear mixer to achieve a desired particle size and viscosity.

In the first stage of the lysed cell suspension production (shown in FIG. 3), a pre-weighed amount of rapeseed oil (30 kg, which is about 20 wt. % of the final lysed cell in oil suspension) and portions of pre-weighted amount (120 kg, which is 80 wt. % of the final lysed cell in oil suspension) of microalgal cells (i.e., microbial cell matter) were added into the low shear mixer. Not all of the microalgal cells were dosed into the oil at one time due to the increase in viscosity which renders the operation of the low shear mixer difficult. Instead, the microalgal cells were added in portions into the oil, and the mixture was recirculated into the low shear mixer until the mixture became too viscous to further incorporate additional portions of the microalgal cells. In one trial, the microalgal cell/oil mixture became too viscous to pump and pass through the low shear mixer when approximately 60 kilograms of microalgal cells were incorporated into 30 kilograms of oil. In this particular trial, the 60 kilograms of microalgal cells were incorporated into the oil in four or five separate portions. After each portion of microalgal cells was incorporated into the mixture, the mixture was passed through the low shear mixer between 1 to 10 times before another portion of microalgal cells was incorporated into the mixture. By the time that approximately 60 kilograms of microalgal powder was incorporated into 30 kilograms of oil, approximately 20% cell lysis was observed in the cell and oil mixture.

The cell and oil mixture with partial cell lysis was then fed into the high shear mixer to further lyse the cells to reduce the viscosity of the mixture so that additional portions of microalgal cells could be added into the partially lysed cell suspension. See FIG. 4. The partially lysed cell suspension was passed through the high shear mixer about 10 times, during which variable energy input was provided. After the viscosity of the lysed cell suspension was reduced to add further portions of microalgal cells, the further lysed cell suspension was returned to a process tank so that it could pass through the low shear mixer with further portions of microalgal cells.

After the high shear mixer step and before returning the lysed cell suspension to the low shear mixer to further incorporate additional portions of microalgal cells, the cell suspension was passed through the heat exchanger in which the temperature was kept below 50° C. The high shear mixer could increase the temperature of the suspension which could affect stability of valuable biomaterial in the suspension. One or more pumps were also added throughout the system to invoke the recycle flow and to set the recycle flow independently from other pieces of equipment in the recycle loop. The addition of vacuum pumps could also assist in removing air bubbles to improve oxidative stability of the lysed cell suspension.

Once returned to the low shear mixer, the remaining microalgal cells were added in portions to the further lysed cell in oil suspension. In one trial, the remaining portions of the microalgal cells were added in 4-5 increments to incorporate the entire batch of the pre-weighed microalgal cells into the further lysed cell in oil suspension. After each portion of microalgal cells was added, the further lysed cell suspension in oil passed through the low shear mixer between 1 to 10 times before the next portion of microalgal cells was added. After all of the pre-weighted microalgal cells were incorporated into the further lysed cell in oil suspension, it was returned to the high shear mixer to further lyse the cells to reduce the viscosity and particle size of the cells in the suspension.

In the high shear mixer, the further lysed cell suspension was passed through the high shear mixer multiple times to reduce the viscosity and the particle size of the cells in the suspension. In one trial, the lysed cell suspension recirculated into the high shear mixer approximately 25 times until a desired particle distribution size and viscosity were achieved.

Several trials were performed using similar processes described above, and with a higher cell loading (i.e., 80 wt. % microalgal cell matter and 20 wt. % oil) in the lysed cell suspension, the viscosity of the cell suspension was approximately 1.05 g/ml. The particle size Dv90 value of the final lysed cell suspension generally ranged from 139 microns to 192 microns between different trials. The particle size Dv50 value of the final lysed cell suspension generally ranged from 53 microns to 77 microns between different trials. The particle size distribution of the lysed cell in oil suspension had a bimodal curve with two peaks. See FIG. 2. The smaller peak of the two peaks had a particle size Dv50 value ranging from 3 to 6 microns, and the larger peak of the two peaks had a particle size Dv50 value ranging from 80 to 200 microns.

The degree of cell lysis in the suspension ranged between 80% to 98%.

In one trial, the total energy input (to the low shear mixer, the high shear mixture, and pump) to generate the final lysed cell suspension was approximately 0.1198 kW*Hr/kg. In the context of total energy input, kilograms of weight refers to the weight of both biomass and oil in the system.

An exemplary system for producing a suspension comprising lysed cells in oil is illustrated in FIGS. 3-5. As shown in the figures, Powder hopper 11 is provided to add microbial cell matter into the system. Oil is provided to vessel 2 with mixer 1, assisted by the provision of vacuum through pump 6. Disperser 12 (a low shear mixer such as YTRON-ZC) is used to incorporate and disperse microbial cell matter into a carrier oil which is generally added to vessel 2 with a mixer 1. Pump 10 can assist in invoking recirculation of the material throughout the system. Cooler 14 can be added, e.g., after the high shear mixer 13 (such as YTRON-Z) to dissipate heat generated by the high shear mixer and other equipment. Inert gas, e.g., nitrogen or argon, 7 can be purged into the product container 15 to reduce oxidation of the suspension. Vacuum pump 6 can be added to assist incorporation of the microbial cell matter into carrier oil as well as to remove any air bubbles. Valve 5 can be used for sampling. Valve 8 can be used to control the flow of the material and change the process configuration. Temperature sensor 3 and pressure sensor 4 can be also added to the system.

Example 5. Concurrent Uses of Two Different
Types of Shear Mixers to Produce a Suspension
Comprising Lysed Cells in Oil Instead of recycling the mixture of microbial cell matter and oil alternatively over YTRON-Zc powder dispensing system and YTRON-Z high shear mixer, in this example, both pieces of equipment were used concurrently in the same loop to produce a suspension comprising lysed cells in oil as shown in FIG. 5. In this example, the preweighted microalgal cell matter (137.6 kg) from Example 1 was divided into nine equal portions. The portions were added in increments to 30 kg of carrier oil over the course of about 21 minutes while being recirculated through both YTRON-Zc powder dispersing system and YRON-Z high shear mixer. After all of the preweighed microalgal cell matter was added to the carrier oil, the mixture was continually recirculated through both pieces of equipment for another 43 minutes until an acceptable particle size distribution and cell lysis. In this example, at least 75% cell lysis was achieved. The total energy input (the low shear mixer, the high shear mixture, and pump) to generate the final lysed cell suspension was approximately 0.1496 kW*Hr/kg.

WO2018005856 (and its US equivalent, US20180000130) and all other publications cited in this application are incorporated herein by reference for all purposes.

It is understood that the examples and embodiments described herein are not intended to limit the scope of the invention. Various modifications, alternative constructions and equivalents may be employed without departing from the scope of the appended claims. Moreover, one or more features or steps of any embodiments may be combined with any other features or steps of any other embodiments in any manner without departing from the scope of the present invention.

The invention claimed is:

1. A process for manufacturing a lysed cell in oil suspension with a solids content of at least 10 wt. %, a water content of at most 10 wt. %, and a bimodal particle size distribution with a first peak having a Dv50 value of 3 to 6 microns, and a second peak having a Dv50 value of 80 to 200 microns, the process comprising:
(a) adding a first portion of microbial cell matter comprising cells to an oil to provide a mixture,
(b) subjecting the mixture of microbial cell matter and oil to one or more shear steps to effect lysis of at least part of the cells and produce a first lysed cell in oil suspension comprising lysed cells in oil,
(c) adding a further portion of microbial cell matter comprising cells to the first lysed cell in oil suspension to provide a mixture, and
(d) subjecting the mixture of microbial cell matter and the first lysed cell in oil suspension to one or more shear steps to effect lysis of at least part of the cells and produce a second lysed cell in oil suspension comprising lysed cells in oil.

2. The process according to claim 1, further comprising:
(e) adding a further portion of microbial cell matter comprising cells to the second lysed cell in oil suspension to provide a mixture, and
(f) subjecting the mixture of microbial cell matter and the second lysed cell in oil suspension to one or more shear steps to effect lysis of at least part of the cells and produce a further third lysed cell in oil suspension comprising lysed cells in oil.

3. The process according to claim 1, wherein at least the final shear step is carried out to effect at least 70% lysis, at least 75% cell lysis, at least 80% cell lysis, at least 85% cell lysis, at least 90% cell lysis, or at least 95% cell lysis in the second lysed cell in oil suspension after the final shear step.

4. The process according to claim 1, wherein at least the first shear step is carried out to effect 1-60% cell lysis, 5-50% cell lysis, 10-40% cell lysis, 15-30% cell lysis, or 15-25% cell lysis, calculated on the product resulting from the step.

5. The process according to claim 1, wherein the final shear step is carried out at a higher shear than the first shear step.

6. The process according to claim 1, which is a continuous process, optionally wherein the process has a capacity of greater than 5,000 kg/h of cell matter intake.

7. A lysed cell in oil suspension having a solids content of at least 10 wt. %, a water content of at most 10 wt. %, and a bimodal particle size distribution with a first peak having a Dv50 value of 3 to 6 microns, and a second peak having a Dv50 value of 80 to 200 microns, wherein the suspension comprises lysed cell matter and oil.

8. The lysed cell in oil suspension according to claim 7, further comprising an antioxidant.

9. The lysed cell in oil suspension according to claim 7, wherein the suspension which has a DHA content of at least 10 wt. % or between 20 wt. % and 45 wt. %.

10. The lysed cell in oil suspension according to claim 1, wherein the suspension has a water content of at most 6 wt. %.

11. A composition comprising the lysed cell in oil suspension of claim 7 and one or more components of a feed or food product.

12. A process for manufacturing an impregnated pellet, wherein a porous pellet is contacted with the lysed cell in oil suspension of claim 7, wherein the porous pellet is formulated as an aquaculture feed pellet.

13. A feed product comprising the lysed cell in oil suspension of claim 7.

14. A method of raising an animal comprising feeding an animal the feed product of claim 13.

15. A method of sustainably producing a meat product by feeding an animal the feed product of claim 13, wherein the meat product comprises an increased level of omega-3 fatty acids compared to the meat product produced without feeding the animal the composition comprising the lysed cell in oil suspension.

16. The lysed cell in oil suspension according to claim 7, wherein the suspension has a solids content of at least 15 wt. %.

17. The lysed cell in oil suspension according to claim 10, wherein the suspension has a water content of at most 4 wt. %.

18. The lysed cell in oil suspension according to claim 17, wherein the suspension has a water content of at most 2 wt. %.

19. The lysed cell in oil suspension according to claim 18, wherein the suspension has a water content of at most 1.0 wt. %.

* * * * *